United States Patent
Ishikawa

(10) Patent No.: US 8,986,481 B2
(45) Date of Patent: Mar. 24, 2015

(54) MANUFACTURING METHOD AND MANUFACTURING EQUIPMENT OF COMPOSITE SHEET

(75) Inventor: Shinichi Ishikawa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 164 days.

(21) Appl. No.: 13/124,588

(22) PCT Filed: Sep. 10, 2009

(86) PCT No.: PCT/JP2009/065833
§ 371 (c)(1),
(2), (4) Date: Jul. 8, 2011

(87) PCT Pub. No.: WO2010/044324
PCT Pub. Date: Apr. 22, 2010

(65) Prior Publication Data
US 2011/0259504 A1    Oct. 27, 2011

(30) Foreign Application Priority Data
Oct. 15, 2008   (JP) ................ 2008-266717

(51) Int. Cl.
*B29C 65/56*   (2006.01)
*B65H 37/04*   (2006.01)
*A61F 13/15*   (2006.01)

(52) U.S. Cl.
CPC .......... *B65H 37/04* (2013.01); *A61F 13/15609* (2013.01); *B65H 2801/57* (2013.01)
USPC ............................. 156/163; 156/229

(58) Field of Classification Search
USPC ............... 156/163, 229, 494, 73.6, 436, 164
See application file for complete search history.

(56) References Cited

U.S. PATENT DOCUMENTS

| 5,275,676 A * | 1/1994 | Rooyakkers et al. ......... 156/164 |
| 6,287,409 B1 | 9/2001 | Stephany |
| 6,589,149 B1 * | 7/2003 | VanEperen et al. .......... 493/380 |

FOREIGN PATENT DOCUMENTS

| JP | 63-97565 A | 4/1988 |
| JP | 03-000409 A | 1/1991 |

(Continued)

OTHER PUBLICATIONS

ISR for PCT/JP/2009/065833 dated Dec. 22, 2009.
Chinese Office Action for Application No. 200980140847.7 mailed Jan. 7, 2013.

(Continued)

*Primary Examiner* — Jacob T Minskey
*Assistant Examiner* — Vishal I Patel
(74) *Attorney, Agent, or Firm* — Lowe Hauptman & Ham, LLP

(57) ABSTRACT

A manufacturing method of a composite sheet includes: bonding a belt member to a sheet surface of the belt-like sheet by supplying a belt-like sheet to an outer circumferential surface of a bonding roll; supplying the belt member to a part of the belt-like sheet that is brought in contact with the outer circumferential surface of the bonding roll and overlapping the belt member to the part. The guide member has a reciprocating roller and a supply roller. The method further includes wrapping the belt member subsequently around the outer circumferential surface of the supply roller and the outer circumferential surface of the reciprocating roller, and leading the belt member to the belt-like sheet; and oscillating the supply roller so that the outer circumferential surface of the supply roller faces toward the reciprocating roller in accordance with a reciprocating motion of the reciprocating roller.

19 Claims, 6 Drawing Sheets

(56) References Cited

FOREIGN PATENT DOCUMENTS

| | | |
|---|---|---|
| JP | 03-000409 | 7/1991 |
| JP | 11-322147 | 11/1999 |
| JP | 11-322147 A | 11/1999 |
| JP | 2002-128345 A | 5/2002 |
| JP | 2003-517880 A | 6/2003 |
| JP | 2004-505725 A | 2/2004 |
| JP | 2004-159866 A | 6/2004 |

OTHER PUBLICATIONS

Office Action as issued on Mar. 25, 2013, in corresponding Japanese Patent Application.

Office Action mailed Oct. 15, 2013, corresponds to Japanese patent application No. 2008-266717.

Office Action dated Nov. 4, 2013, corresponds to Chinese patent application No. 200980140847.7.

* cited by examiner

MANUFACTURING METHOD AND MANUFACTURING EQUIPMENT OF COMPOSITE SHEET

RELATED APPLICATIONS

The present application is National Phase of PCT/JP2009/065833, filed Sep. 10, 2009, and claims priority from Japanese Application Number 2008-266717 filed Oct. 15, 2008.

TECHNICAL FIELD

The present invention relates to manufacturing methods and manufacturing equipments of composite sheets by bonding to a belt-like sheet that is transported in a transporting direction an elastic belt member in a predetermined serpentine pattern.

BACKGROUND ART

In the past, in a manufacturing line of an absorbent article such as a disposable diaper, on a sheet surface of a belt-like sheet that is transported continuously in the transporting direction, an elastic member is continuously attached in a serpentine pattern such as a sine curve.

As such a method, patent literature 1 describes that an oscillating am that oscillates in an intersecting direction that intersects with the transporting direction of the belt-like sheet is closely arranged in a transporting path of the belt-like sheet, and on the other hand an elastic member is passed through a through hole at an oscillating end of the oscillating arm, so as to make the elastic member oscillate and be attached to the belt-like sheet.

Further, in patent literature 2, there is disclosed that the elastic member is put around a rolling roller that rolls around an outer circumferential surface of a transfer roller and makes the rolling roller reciprocate in an axial direction of the transfer roller, in order to make the elastic member be adsorbed and held on the outer circumferential surface of the transfer roller in a serpentine pattern such as a sine curve, and thereafter the belt-like sheet is made to come into contact with the outer circumferential surface of the transfer roller and the elastic member is transferred to the belt-like sheet and attached thereon.

CITATION LIST

Patent Literature

PTL 1: JP-A-2004-159865
PTL 2; JP-A-2003-517880

SUMMARY OF INVENTION

Technical Problem

In the case where a belt member having a wide width is used as the above-described elastic member, however, with the method of the above patent literature 1, the elastic member bends when passing the through hole at the oscillating end, and therefore it becomes difficult to make the elastic member surface contact the belt-like sheet and be attached thereto.

On the other hand, with the method in patent literature 2, the elastic member is put around the outer circumferential surface of the rolling roller, so that the elastic member can be maintained in a flat state and transferred to the transfer roller. As a result the elastic member can surface contact the belt-like sheet and be attached thereto.

With the reciprocating motion of the rolling roller, however, the traveling state of the elastic member may become unstable in the rolling roller. Then, not only does the attachment precision to a target bonding position on the belt-like sheet decrease, but in the worst case the elastic member may fall off the rolling roller. Such a danger increases particularly in the case a soft material such as a nonwoven cloth is used as the elastic member, or the rolling roller is reciprocated at high speed in order to increase processing ability.

Further, internal force is present due to the serpentine pattern in the elastic member held on the outer circumferential surface of the transfer roller, therefore if the elastic member is not firmly adsorbed on the outer circumferential surface the serpentine pattern will break up. In regards to this point, in the case the elastic member is an air permeable material such as a nonwoven cloth it becomes hard to be adsorbed, but at present there is found no effective holding means other than being adsorbed. That is, it is difficult to stably hold the elastic member in a serpentine pattern on the outer circumferential surface of the transfer roller.

The present invention has been made in view of the above problems, and it is an object to provide, in a manufacturing method and manufacturing equipment of a composite sheet by bonding to a sheet surface of a belt-like sheet that is transported continuously in a predetermined transporting direction, a belt member in a serpentine pattern by reciprocating a roller to which an elastic belt member has been put around in an intersecting direction that intersects the transporting direction, a manufacturing method and manufacturing equipment of a composite sheet in which a transfer roller can be provided and stability of the traveling state of a belt member in the roller can be provided.

Solution to Problem

As aspect of the invention is a manufacturing method of a composite sheet that continuously supplies, to a sheet surface of a belt-like sheet that is transported continuously in a predetermined transporting direction, an elastic belt member while reciprocating the belt member in an intersecting direction that intersects the transporting direction, and thus bonds the belt member to the sheet surface of the belt-like sheet while continuously changing a bonding position of the belt member on the sheet surface in the intersecting direction, the method comprising:

causing the belt member to surface contact with the sheet surface of the belt-like sheet and to bond thereto, by supplying the belt-like sheet to an outer circumferential surface of a bonding roll that rotates in a direction along the transporting direction, and supplying the belt member via a guide member to a part of the belt-like sheet that is brought in contact with the outer circumferential surface of the bonding roll and overlapping the belt member to the part, the guide member having a reciprocating roller that reciprocates in the intersecting direction and a supply roller that is provided at a predetermined position and to which the belt member is supplied to;

wrapping the belt member subsequently around the outer circumferential surface of the supply roller and the outer circumferential surface of the reciprocating roller and leading the belt member to the belt-like sheet;

oscillating the supply roller so that the outer circumferential surface of the supply roller faces toward the reciprocating roller in accordance with a reciprocating motion of the reciprocating roller.

A further aspect of the invention is a manufacturing equipment of a composite sheet that continuously supplies, to a sheet surface of a belt-like sheet that is transported continuously in a predetermined transporting direction, an elastic belt member while reciprocating the belt member in an intersecting direction that intersects the transporting direction, and thus bonds the belt member to the sheet surface of the belt-like sheet while continuously changing a bonding position of the belt member on the sheet surface in the intersecting direction, the equipment comprising:

a bonding roll that rotates in a direction along the transporting direction and an outer circumferential surface thereof to which the belt-like sheet is brought in contact with; and a guide member that causes the belt member to surface contact with the sheet surface of the belt-like sheet and to bond thereto, by supplying the belt member to a part of the belt-like sheet that is brought in contact with the outer circumferential surface of the bonding roll and overlapping the belt member to the part, the guide member having a reciprocating roller that reciprocates in the intersecting direction and a supply roller that is provided at a predetermined position and to which the belt member is supplied to, the belt member being subsequently wrapped around the outer circumferential surface of the supply roller and the outer circumferential surface of the reciprocating roller and the belt member being led to the belt-like sheet, the supply roller being oscillated so that the outer circumferential surface of the supply roller faces toward the reciprocating roller in accordance with a reciprocating motion of the reciprocating roller.

Other features of the present invention will be made clear by the present specification with reference to the accompanying drawings.

Effects of Invention

According to this invention, it is possible to omit the transfer roller, and to provide stability in the traveling state of the belt member.

DESCRIPTION OF EMBODIMENTS

Figure 1A:
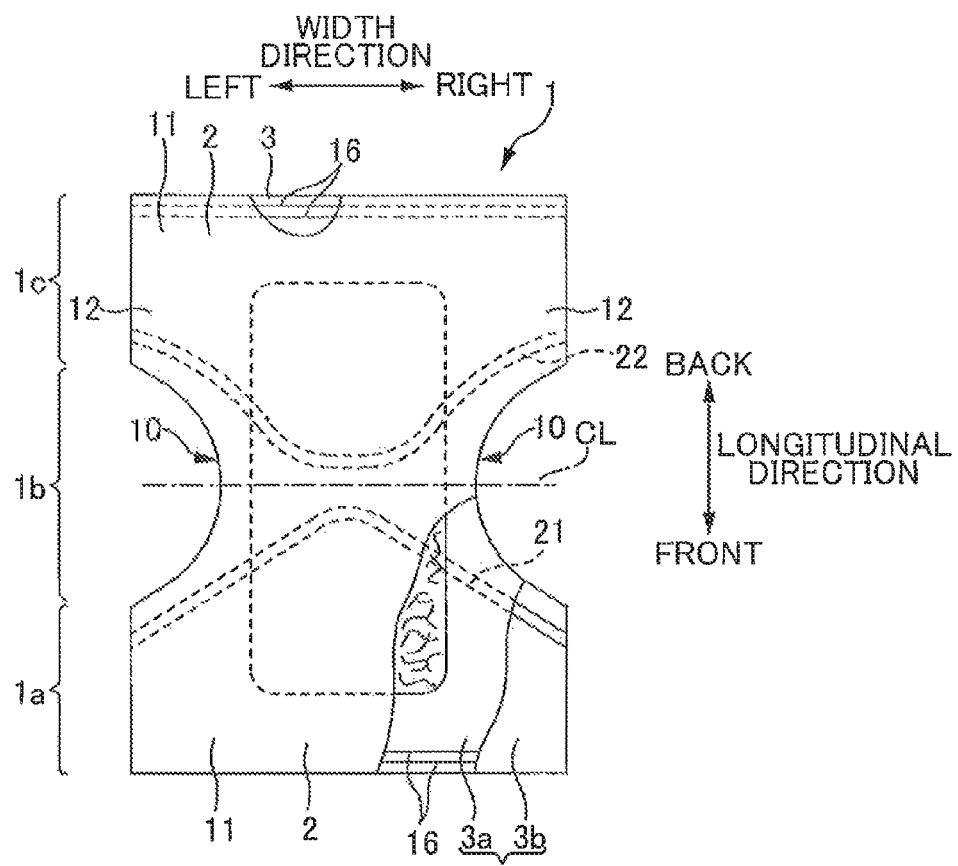
FIG. 1A is a partially cutaway plan view of a diaper 1.

At least the following matters will become clear through the description of the present specification and the accompanying drawings.

A manufacturing method of a composite sheet that continuously supplies, to a sheet surface of a belt-like sheet that is transported continuously in a predetermined transporting direction, an elastic belt member while reciprocating the belt member in an intersecting direction that intersects the transporting direction, and thus bonds the belt member to the sheet surface of the belt-like sheet while continuously changing a bonding position of the belt member on the sheet surface in the intersecting direction, the method comprising:

causing the belt member to surface contact with the sheet surface of the belt-like sheet and to bond thereto, by supplying the belt-like sheet to an outer circumferential surface of a bonding roll that rotates in a direction along the transporting direction, and supplying the belt member via a guide member to a part of the belt-like sheet that is brought in contact with the outer circumferential surface of the bonding roll and overlapping the belt member to the part, the guide member having a reciprocating roller that reciprocates in the intersecting direction and a supply roller that is provided at a predetermined position and to which the belt member is supplied to;

wrapping the belt member subsequently around the outer circumferential surface of the supply roller and the outer circumferential surface of the reciprocating roller and leading the belt member to the belt-like sheet;

oscillating the supply roller so that the outer circumferential surface of the supply roller faces toward the reciprocating roller in accordance with a reciprocating motion of the reciprocating roller.

According to such a manufacturing method of a composite sheet, the outer circumferential surface of the supply roller faces the reciprocating roller according to the reciprocating motion of the reciprocating roller. Thus, even if the reciprocating roller changes position in the intersecting position by the reciprocating motion, the belt member can be surely transported toward the reciprocating roller, and as a result the traveling state of the belt member can be stabilized, such as the falling off of the belt member from the reciprocating roller can be effectively prevented.

Further, since the transfer roller is not used, even in the case that the belt member is an air permeable material the belt member can be bonded to the strip sheet without any inconvenience.

In a manufacturing method of a composite sheet, preferably an oscillating motion of the supply roller is performed with a predetermined support axis as a rotational center, and the rotation center line of the support axis is in contact with the outer circumferential surface of the supply roller.

According to such a manufacturing method of a composite sheet, a travel amount of the supply roller in the intersecting direction that may occur with the oscillating motion of the supply roller can be kept to a minimum, therefore the traveling state of the belt member can be stabilized, such as the falling off of the belt member from the supply roller can be effectively prevented.

In a manufacturing method of a composite sheet, preferably the belt member is supplied to the supply roller along the rotation center line of the support axis.

According to such a manufacturing method of a composite sheet, a wraparound angle of the belt member to the supply roller can be largely ensured.

In a manufacturing method of a composite sheet, preferably the guide member has an oscillating arm that oscillates in the intersecting direction with the support axis as a center of rotation, the reciprocating roller is provided at an oscillating end of the oscillating arm along with the supply roller provided to a part of the oscillating arm near to the support axis than the oscillating end, and the reciprocating roller reciprocates in the intersecting direction by the oscillating motion of the oscillating arm, and the supply roller is oscillated so that the outer circumferential surface of the supply roller faces toward the oscillating end of the oscillating arm in accordance with the oscillating motion of the oscillating arm.

According to such a manufacturing method of a composite sheet, the outer circumferential surface of the supply roller according to the oscillating motion of the oscillating arm faces toward the oscillating end, namely the reciprocating roller. Thus, even if the reciprocating roller changes position in the intersecting direction according to the oscillating motion of the oscillating arm, the belt member can be surely transported toward the reciprocating roller. Thus, the traveling state of the belt member can be stabilized, such as the falling off of the belt member from the reciprocating roller can be effectively prevented.

In a manufacturing method of a composite sheet, preferably the supply roller is supported on the oscillating arm in a state the outer circumferential surface of the supply roller is facing toward the oscillating end of the oscillating arm with an orientation to the oscillating arm that is unchangeable.

According to such a manufacturing method of a composite sheet, the outer circumferential surface of the supply roller can be made to always face the oscillating end, by completely synchronizing with the oscillating motion of the oscillating arm. The supply roller oscillates by the oscillating arm, so an actuator to oscillate the supply roller does not have to be separately provided, and the equipment configuration can be simplified.

In a manufacturing method of a composite sheet, preferably the reciprocating roller and the supply roller are arranged on a line connecting the oscillating end and the support axis of the oscillating arm, and the reciprocating roller is supported on the oscillating arm in a state the outer circumferential surface of the reciprocating roller is facing toward the support axis and with an orientation to the oscillating arm that is unchangeable.

According to such a manufacturing method of a composite sheet, it is possible to make the outer circumferential surface of the reciprocating roller always face toward the support axis, by completely synchronizing with the oscillating motion of the oscillating arm. Thus, the tension difference of both end edges of the belt member in the width direction that may occur with the reciprocating motion of the reciprocating roller can be surely relaxed and reduced. Thus, the traveling state of the belt member can be stabilized, such as the falling off of the belt member from the reciprocating roller can be effectively prevented.

In a manufacturing method of a composite sheet, preferably the reciprocating roller is supported on the oscillating arm with an orientation of the outer circumferential surface of the reciprocating roller toward the oscillating end that is changeable, and the orientation can be changed in accordance with a tension from the belt member that has been wrapped around the reciprocating roller.

According to such a manufacturing method of a composite sheet, the orientation of the reciprocating roller changes according to the tension from the belt member, and undue load acting from the reciprocating roller to the belt member can be effectively suppressed, and a bias in a tension distribution of the belt member in the width direction can be effectively reduced.

In a manufacturing method of a composite sheet, preferably the intersecting direction is perpendicular to the transporting direction, the support axis is perpendicular to a rotation axis that rotates the bonding roll in a direction along the transporting direction, a rotation axis of the reciprocating roller and a rotation axis of the supply roller are arranged so that a surface depicted by the rotation axis of the reciprocating roller and the rotation axis of the supply roller with the oscillating motion of the oscillating arm is parallel to the rotation axis of the bonding roll.

According to such a manufacturing method of a composite sheet, the rotation axis of the bonding roll is arranged in an orientation parallel to a surface depicted by the rotation axis of the reciprocating roller and the rotation axis of the supply roller by the oscillating motion of the oscillating arm. Thus, twisting of the belt member when the belt member is handed over from the reciprocating roller to the bonding roll can be suppressed, and the belt member can surely be surface contacted to the sheet surface of the belt-like sheet.

In a manufacturing method of a composite sheet, preferably the reciprocating roller and the supply roller are each a roller with a crown with a maximum diameter part of each roller set in a central portion in a width direction.

According to such a manufacturing method of a composite sheet, the travel position of the belt member can be stabilized to a central portion in the width direction of the reciprocating roller and the supply roller, and thus the traveling state of the belt member in the reciprocating roller and the supply roller can be stabilized.

In a manufacturing method of a composite sheet, preferably a wraparound angle of the belt member to the outer circumferential surface of the reciprocating roller is equal to or greater than 90 degrees.

According to such a manufacturing method of a composite sheet, the wraparound angle of the belt member to the outer circumferential surface of the reciprocating roller is made equal to or greater than 90 degrees, so the belt member can be firmly held on the outer circumferential surface. Thus the traveling state of the belt member can be stabilized, such as the falling off of the belt member from the reciprocating roller can be prevented.

In a manufacturing method of a composite sheet, preferably the belt member is reversed in the traveling direction by the reciprocating roller and is supplied to the bonding roll.

According to such a manufacturing method of a composite sheet, the wraparound angle to the reciprocating roller can be largely ensured.

In a manufacturing method of a composite sheet, preferably a wraparound start position of the belt-like sheet to the bonding roll is positioned in between the reciprocating roller and the supply roller.

According to such a manufacturing method of a composite sheet, it is possible that, by the reciprocating roller, the traveling direction of the belt member is reversed and the belt member is supplied to the bonding roll.

In a manufacturing method of a composite sheet, preferably the intersecting direction is perpendicular to the transporting direction, the support axis is perpendicular to a rotation axis that rotates the bonding roll in a direction along the transporting direction, the reciprocating roller is arranged so that a rotation axis of the reciprocating roller is perpendicular to the support axis, and the supply roller is arranged so that the rotation axis of the supply roller is perpendicular to the support axis.

According to such a manufacturing method of a composite sheet, the orientation of the rotation axes of the bonding roll, the reciprocating roller, and the supply roller are each in a perpendicular relationship with the support axis. Thus, twisting of the belt member when the belt member is handed over from the reciprocating roller to the bonding roll can be suppressed, and the belt member can be surely surface contacted to the sheet surface of the belt-like sheet.

A manufacturing equipment of a composite sheet that continuously supplies, to a sheet surface of a belt-like sheet that is transported continuously in a predetermined transporting direction, an elastic belt member while reciprocating the belt member in an intersecting direction that intersects the transporting direction, and thus bonds the belt member to the sheet surface of the belt-like sheet while continuously changing a bonding position of the belt member on the sheet surface in the intersecting direction, the equipment comprising:

a bonding roll that rotates in a direction along the transporting direction and an outer circumferential surface thereof to which the belt-like sheet is brought in contact with; and a guide member that causes the belt member to surface contact with the sheet surface of the belt-like sheet and to bond thereto, by supplying the belt member to a part of the belt-like sheet that is brought in contact with the outer circumferential surface of the bonding roll and overlapping the belt member to the part, the guide member having a reciprocating roller that reciprocates in the intersecting direction and a supply roller that is provided at a predetermined position and to which the belt member is supplied to, the belt member being subsequently wrapped around the outer circumferential surface of the supply roller and the outer circumferential surface of the reciprocating roller and the belt member being led to the belt-like sheet, the supply roller being oscillated so that the outer circumferential surface of the supply roller faces toward the reciprocating roller in accordance with a reciprocating motion of the reciprocating roller.

According to such a manufacturing apparatus of a composite sheet, the outer circumferential surface of the supply roller faces the reciprocating roller according to the reciprocating motion of the reciprocating roller. Thus, even if the reciprocating roller changes position in the intersecting position by the reciprocating motion, the belt member can be surely transported toward the reciprocating roller, and as a result the travel state of the belt member can be stabilized, such as the falling off of the belt member from the reciprocating roller can be effectively prevented.

Further, since the transfer roller is not used, even in the case that the belt member is an air permeable material, the belt member can be bonded to the belt-like sheet without any inconvenience.

The Present Embodiment

A manufacturing method of a composite sheet according to this embodiment is, for example, performed in a part of a manufacturing line of a pants-type disposable diaper 1.

<<<Regarding Diaper 1>>>

Figure 1B:
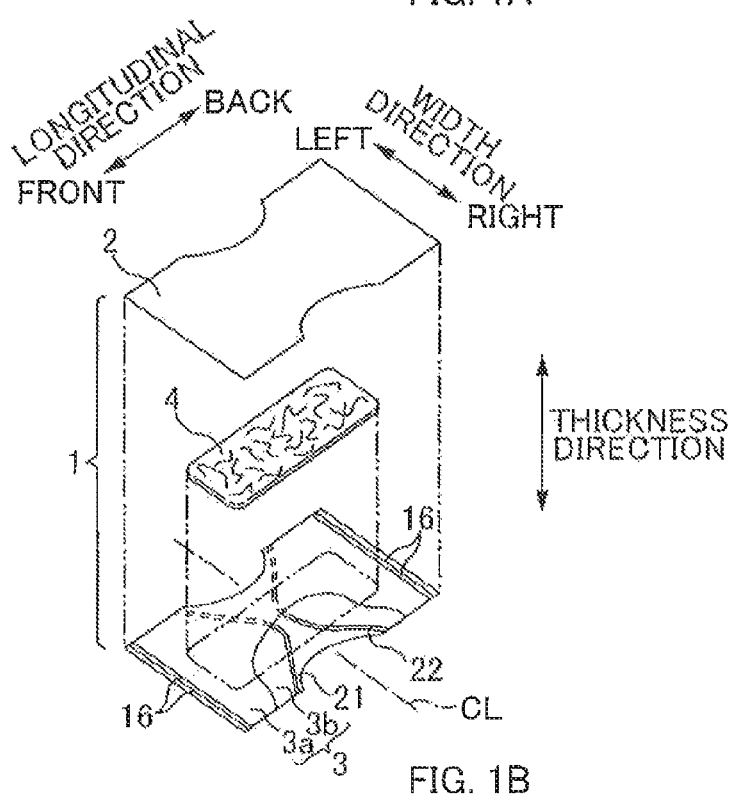
FIG. 1B is an exploded oblique view thereof.

FIG. 1A is a partially cutaway plan view of the diaper 1, and FIG. 1B is an exploded perspective view thereof. Both drawings show an exploded state of the diaper 1 with a front torso area 1a and a back torso area 1c that are separated in a side portion of the paints-type diaper 1.

This diaper 1 has a longitudinal direction, a width direction, and a thickness direction which are orthogonal to each other, and the front torso area 1a, a crotch area 1b, and the back torso area 1c are set along the longitudinal direction of the diaper 1. Further, the diaper 1 has, in the thickness direction, a fluid permeable surface sheet 2, a fluid impermeable back surface sheet 3, and a liquid-absorbent absorbent body 4 that intervenes between these sheets 2, 3. Then, the surface and back surface sheets 2, 3 overlap in portions that extend from peripheral edges of the absorbent body 4, and are bonded to each other by such as a hot-melt adhesive, and thus end edge flaps 11 are formed in the front and back in the longitudinal direction, and side edge flaps 12 are formed in the left and right in the width direction. Note that, in the crotch area 1b of the side edge flaps 12, leg-peripheral recessed portions 10 are curvedly formed inwardly in the width direction, and the diaper 1 has a substantially hourglass shape as a whole.

The lack surface sheet 3 has an inside sheet 3a that faces the surface-sheet 2 and an outside sheet 3b that faces the inside sheet 3a, and these sheets 3a, 3b are the same shape and size, and are bonded to each other by adhering or welding.

The end edge flaps 11 of the front and back torso areas 1a, 1c are each bonded with a torso-peripheral elastic member 16 to the surface and back surface sheets 2, 3 in an extended state.

Further, in the crotch area 1b and its vicinity, a front elastic belt member 21 and a back elastic belt member 22 are provided across the diaper 1 along the width direction thereof. Each of these elastic belt members 21, 22 are extended in the width direction in a predetermined serpentine pattern that is curved in a convex shape toward a center line CL that substantially halves the diaper 1 to the front and back in the longitudinal direction, and they are intervened in between the inside sheet 3a and the outside sheet 3b configuring the back surface sheet 3, and for example are bonded in an extended state to an inner surface of the outside sheet 3b. Then, with the cooperation of these front and back elastic belt members 21, 22, elasticity is provided around the leg-peripheral recessed portions 10.

Note that, here, a sine curve is illustrated as serpentine patterns of these elastic belt member 21, 22, but the serpentine pattern can be appropriately changed so that the leg-peripheral recessed portions 10 can extend and contract around the leg of the wearer of the diaper.

As the material of the surface sheet 2, for example, a fluid permeable plastic film or a nonwoven cloth can be used. Further, as the inside sheet 3a of the back surface sheet 3, a fluid permeable plastic film or a nonwoven cloth is used, and as the outside sheet 3b, an air permeable nonwoven cloth is used.

<<<A Manufacturing Method of a Composite Sheet According to this Embodiment>>>

Such a diaper 1 is completed by various kinds of structural components being bonded and the like to a base material of the diaper 1 that continuously flows along a manufacturing line. The manufacturing method of the composite sheet according to this embodiment bears one process thereof. Namely, here the method is applied to a process of attaching, in respect to a continuous belt-like sheet 103b (hereinafter, referred to as the belt-like sheet 103b) to be the outside sheet 3b of the above-described back surface sheet 3, a continuous elastic belt member 121 (hereinafter, referred to as the belt member 121) to be the above-described front elastic belt member 21 in the above-described serpentine pattern. Note that, it is clear that the back elastic belt member 22 can be attached by the same method, therefore the explanation thereof is omitted.

Figure 2A:
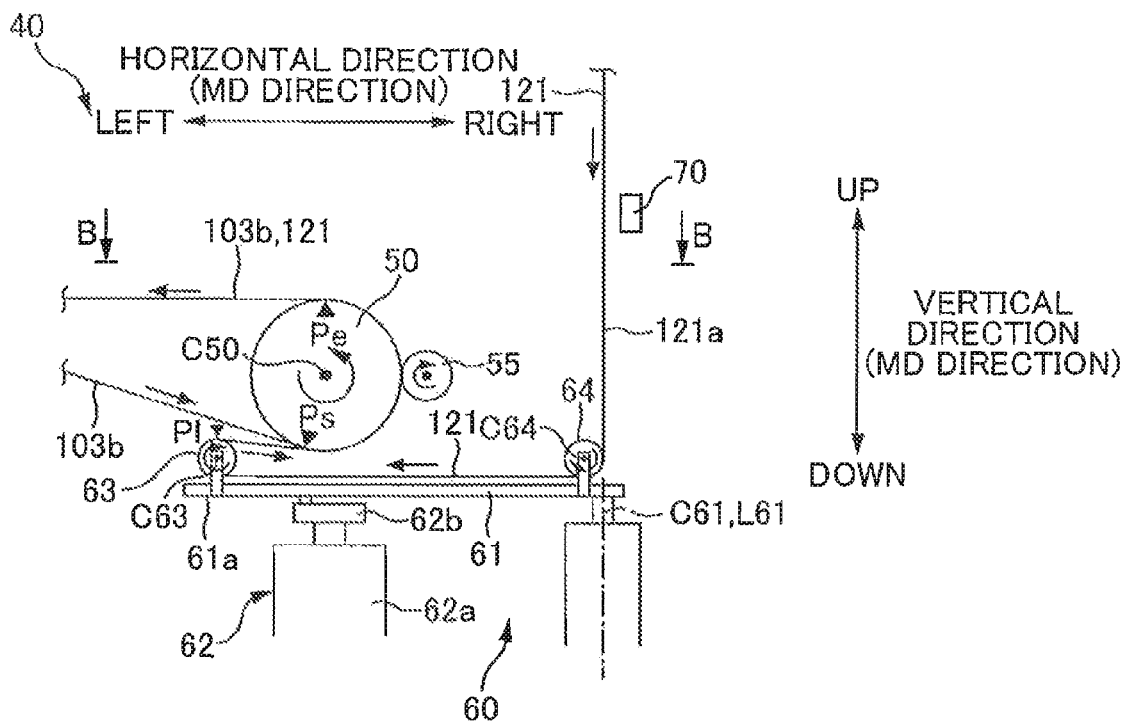
FIG. 2A is a side view of manufacturing equipment 40 of a composite sheet according to the present embodiment.
Figure 2B:
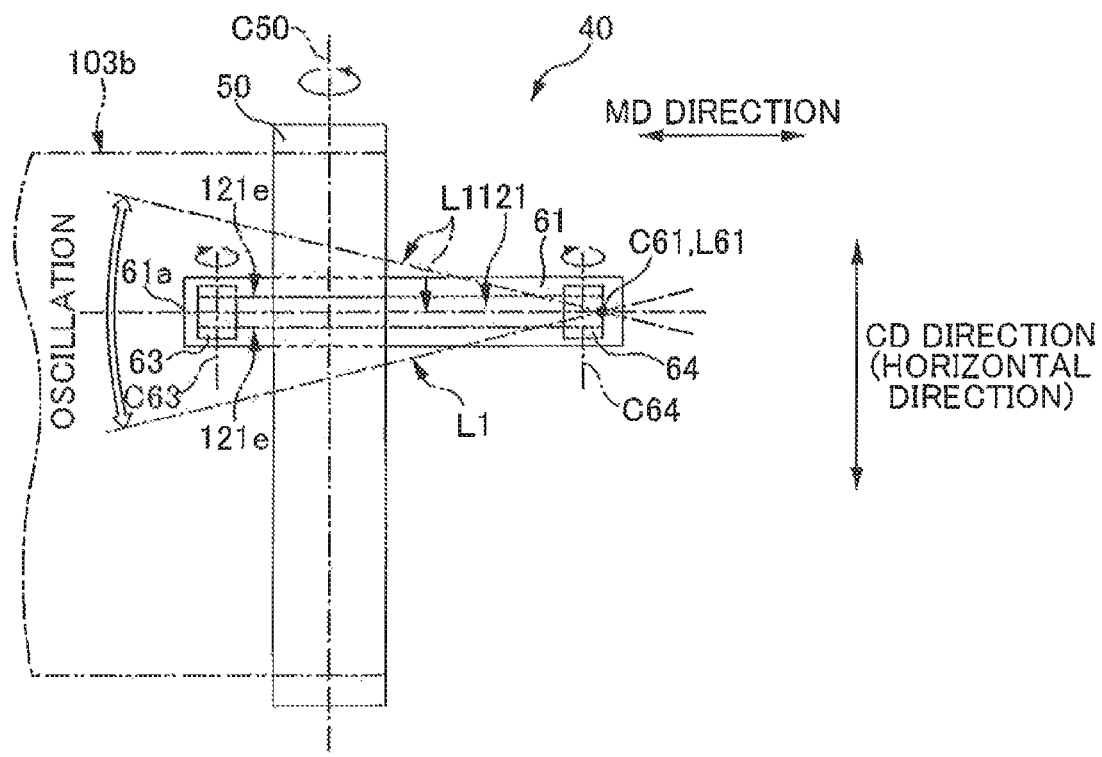
FIG. 2B is a view seen from B-B in FIG. 2A.

FIG. 2A is a side view of the manufacturing apparatus 40 according to this process, and FIG. 2B is a view taken in the direction of arrows B-B in FIG. 2A. Hereinbelow, the width direction of the manufacturing apparatus 40 is referred to as a CD direction, and a direction that intersects with this CD direction is referred to as an MD direction. Namely, the MD direction refers to an arbitrary direction in a plane that intersects the CD direction, and further regarding the MD direction, the two directions that intersect with each other as shown in FIG. 2A are defined as an up-down direction (vertical, direction) and a left-right direction (horizontal direction). The CD direction is also in the horizontal direction, and similarly is in an intersecting relationship with a left-right direction also facing the horizontal direction.

This manufacturing apparatus 40 includes a transport roll 50 (corresponds to a bonding roll), a guide member 60, and an applying device 70. The transport roll 50 transports the belt-like sheet 103b in the MD direction (corresponds to a transporting direction) by wrapping around the belt-like sheet 103b in a predetermined wraparound angle and rotating it. The guide member 60 continuously supplies and bonds the belt member 121 in an extended state to a part of the belt-like sheet 103b that is wrapped around and brought in contact with the outer circumferential surface of the transport roll 50. The applying device 70 applies a hot-melt adhesive to the belt member 121 so as to bond the belt member 121 to the belt-like sheet 103b.

Then, the guide member 60 makes the belt member 121 reciprocate in the CD direction (corresponds to the intersecting direction), while sending the belt member 121 to the belt-like sheet 103b along the MD direction. Thus, the belt member 121 is overlapped and bonded to the sheet surface of the belt-like sheet 103b while the bonding position to the belt-like sheet 103b is momentarily and continuously changed in the CD direction. As a result, the sheet surface of the belt-like sheet 103b is attached with the belt member 121 in a surface contacting state in an intended serpentine pattern such as a sine curve. Hereafter, each structural element 50, 60 is described.

(1) Transport Roll 50

The transport roll 50 has a cylindrical body, as a main body, in which a rotation axis C50 is facing a horizontal CD direction, and the transport roll 50 rotates in a predetermined peripheral speed with a direction along the MD direction as a rotational direction. This transport roll 50 is, for example, supplied with a belt-like sheet 103b substantially horizontally from the left, and the belt-like sheet 103b is wrapped around an outer circumferential surface of the transport roll 50 from an approximately 7 o'clock position at a lower portion of the transport roll 50 as a wraparound start position Ps, at a wraparound angle of for example 180 to 200 degrees and inverted in the transporting direction, and finally is carried out to the right in the substantially horizontal direction with an approximately 12 o'clock position at an upper portion of the transport roll 50 as a wraparound end position Pe.

This transport roll 50 may be configured as a drive roller that drivingly rotates with an appropriate motor and the like as a driving source, or may be configured as a driven roller that is driven and rotated by the belt-like sheet 103b.

Here, preferably, as shown in FIG. 2A, a pressing roller 55 is provided opposed to the outer circumferential surface of the transport roll 50, and the pressing roller 55 may be pressed against the outer circumferential surface of the transport roll 50 with a predetermined pressing power. In this way, with the guide member 60, the bonding strength of the belt member 121 that has been bonded to the belt-like sheet 103b in a desired serpentine pattern can be increased. Note that, in the case the pressing roller 55 rotates at an approximately the same peripheral speed as the transport roll 55, either the driven roller or the driving roller may be used.

(2) Guide Member 60

The guide member 60 has a plate-shaped oscillating arm 61 provided below the transport roll 50. The oscillating arm 61 is arranged so as to straddle the transport roll 50 to the left and right in the horizontal direction. Then, with a support axis C61 positioned to the right than the transport roll 50 as a rotational center, the oscillating end 61a positioned to the left than the transport roll 50 can be oscillated in the CD direction. Note that, as a driving source 62 of the oscillating operation, a configuration with an appropriate motor 62a combined with a clank mechanism 62b and the like can be illustrated.

In the oscillating end 61a, an oscillating end side roller 63 (corresponds to a reciprocating roller) is rotatably supported around a horizontal rotation axis C63, and on the other hand in a part of the oscillating arm 61 near to the support axis C61 than the oscillating end side roller 63, a support axis side roller 64 (corresponds to a supply roller) is rotatably supported about a horizontal rotation axis C64.

Thus, the belt member 121 that is supplied from above from a position to the right than the transport roll 50 downward along the vertical direction is first wrapped around the outer circumferential surface of the support axis side roller 64 and guided to a position to the left than the transport roll 50. Thereafter, the travel direction of the belt member 121 is inverted to the right by the oscillating end side roller 63 in this position, and is supplied from below the transport roll 50 to a wraparound start position Ps of the belt-like sheet 103b.

Then, during this supplying, the oscillating end side roller 63 reciprocates in the CD direction in accordance with the oscillating motion of the oscillating end 61a, and thus, the belt member 121 is bonded, in a desired serpentine pattern on the sheet surface of the belt-like sheet 103b while the bonding position of the belt member 121 in the sheet surface of the belt-like sheet 103b is continuously changed in the CD direction. Further, during supplying, the belt member 121 is constrained, substantially in an even shape by being wrapped around the outer circumferential surface of the support axis side roller 64 and the outer circumferential surface of the oscillating end side roller 63, and therefore is bonded in a surface contacting state in respect to the belt-like sheet 103b.

Here, in this embodiment, the oscillating end side roller 63 and the support axis side roller 64 are each arranged on a line L1 connecting the oscillating end 61a and the support axis C61. Further, the oscillating end side roller 63 is fixedly supported to the oscillating arm 61 in a state where its outer circumferential surface is facing toward the support axis C61 and with an orientation toward the oscillating arm 61 that is unchangeable, and on the other hand the support axis side roller 64 is also fixedly supported to the oscillating arm 61 in a state where its outer circumferential surface is facing toward the oscillating end 61a of the oscillating arm 61 and with an orientation toward the oscillating arm 61 that is unchangeable.

Thus, with this configuration, according to the reciprocating motion of the oscillating end side roller 63, the outer circumferential surface of the support axis side roller 64 is always facing toward the oscillating end side roller 63, so that the belt member 121 can be surely transported toward the oscillating end side roller 63. As a result, the traveling state of the belt member 121 can be stabilized, such as the failing off of the belt member 121 from the oscillating end side roller 63 can be effectively prevented.

Further, according to the above configuration, the rotation axis C63 of the oscillating end side roller 63 and the rotation axis C64 of the support axis side roller 64 are always maintained in a parallel state, regardless of the oscillating motion of the oscillating arm 61. Thus, a tension difference between both end edges in the width direction of the belt member 121 that may occur due to the oscillating motion of the oscillating arm 61 can be surely eased and decreased. As a result, the falling off of the belt member 121 from the oscillating end side roller 63 that may occur due to the oscillating motion may be effectively prevented.

Figure 3A:
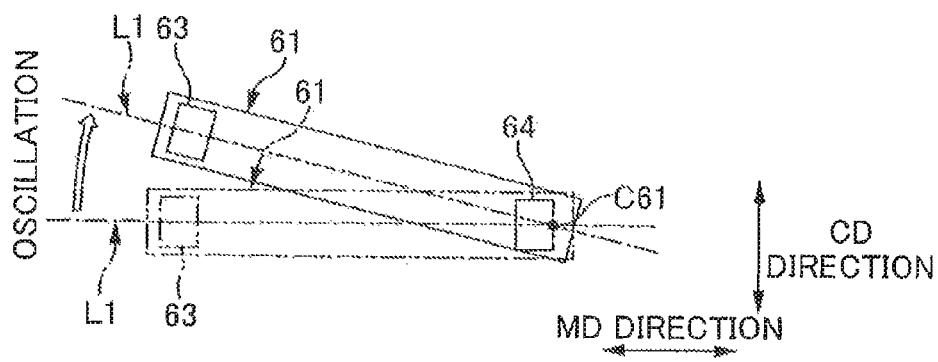
FIG. 3A and FIG. 3B are explanatory views of comparative examples.
Figure 3B:
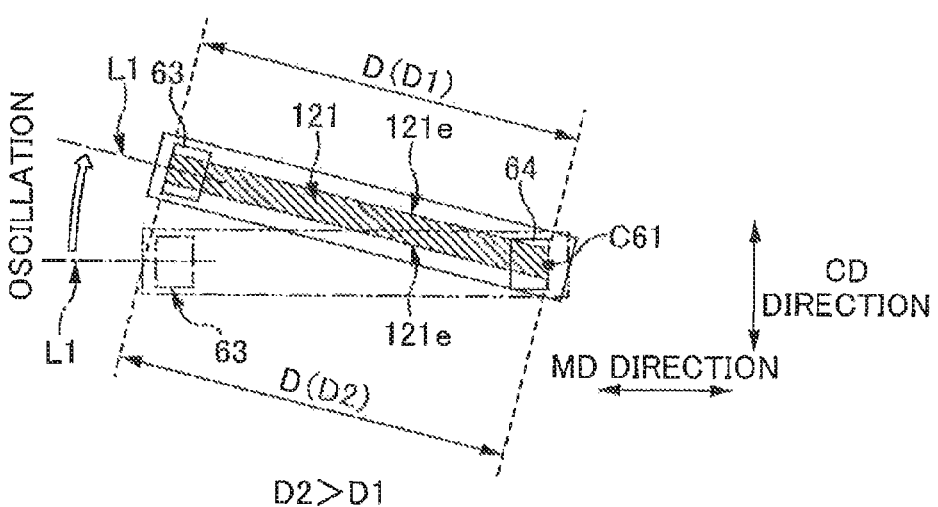
Figure 3C:
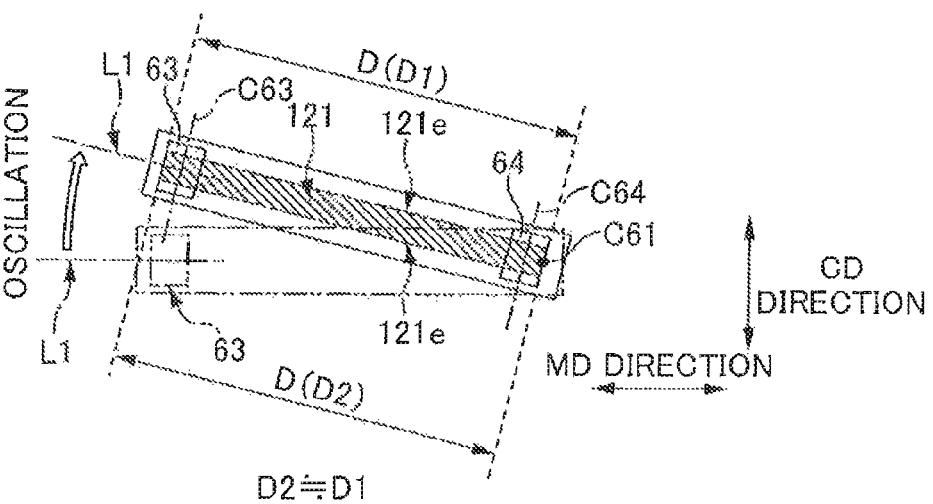
FIG. 3C is an explanatory view of this embodiment.

FIGS. 3A to 3C are the explanatory diagrams. For example, in a configuration such as a comparative example in FIG. 3A, namely, in the case where the oscillating end side roller 63 is fixed to the oscillating arm 61 and an orientation of its outer circumferential surface is considered as integral with the oscillating arm 61, and the support axis side roller 64 is provided with its outer circumferential surface always facing the MD direction regardless of the oscillating motion of the oscillating arm 61, as shown in FIG. 3B, in a state the oscillating arm 61 is oscillated from a parallel state in the MD direction (refer to two dotted chain lines) to a CD direction (refer to solid lines), a wraparound path length D of the belt member 121 between the oscillating end side roller 63 and the support axis side roller 64 will differ between both end edges 121e, 121e of the belt member 121 in the width direction. Namely, in the example in FIG. 3B, D2>D1. Then, resulting from this, a tension difference occurs between both end edges 121e, 121e, and the tension difference changes to a thrust force along a width direction of the belt member 121. Consequently, the belt member 121 side slips on the outer circumferential surfaces of the rollers 63, 64, and in the worst case, the belt member 121 will fall off from these rollers 63, 64.

On the contrary, as in this embodiment shown in FIG. 2B, in the case where the oscillating end side roller 63 and the support axis side roller 64 are fixed to the oscillating arm 61 with the rotational axes C63, C64 thereof in a parallel state, as shown in FIG. 3C, even in a state where the oscillating arm 61 is oscillated in the CD direction, the rotational axes C63, C64 are maintained in a parallel state to each other, so that the wraparound path length D of the belt member 121 between these rollers 63, 64 become substantially equal in both end edges 121e, 121e in the width direction of the belt member 121 (D1≈D2), and tension difference between both end edges 121e, 121e of the belt member 121 generally does not occur. Consequently, the traveling state of the belt member 121 of these rollers 63, 64 is stabilized and the failing off of the belt member 121 is effectively prevented.

In this regard, in this example, as shown in FIG. 2B, the support axis side roller 64 is fixed to the oscillating arm 61, but it may be oscillated independently from the oscillating arm 61 by an appropriate actuator such as a motor. Namely, the rotation axis C64 of the support axis side roller 64 is fixed about the support axis C61 in a manner in which it can oscillate in respect to the oscillating arm 61, and by controlling the above actuator, the support axis side roller 64 may be able to swing so that the outer circumferential surface of the support axis side roller 64 faces the oscillating end 61a of the oscillating arm 61 according to the oscillating motion of the oscillating arm 61, and with this configuration the traveling state of the belt member 121 is stabilized similarly as described above.

On the other hand, the oscillating end side roller 63 does not have to be fixed to the oscillating arm 61, and the rotation axis C63 of the oscillating end side roller 63 may be supported to the oscillating arm 61 so that it can oscillate about an axis that is parallel to the support axis C61. However, in this case, the oscillating end side roller 63 faces an orientation in which there is a balance in a difference in tension in the width direction of the belt member 121 that has been wrapped around thereto, namely, the outer circumferential surface of the oscillating end side roller 63 is in a state in which it is slightly facing the MD direction than in the state in the above FIG. 3C.

Figure 4:
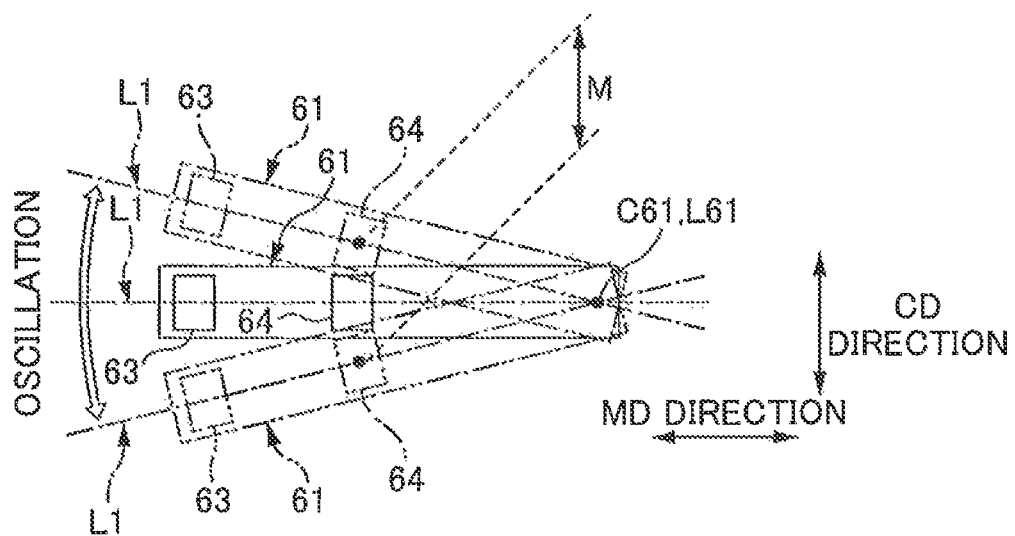
FIG. 4 is a view explaining a preferable reason for a support axis side roller 64 of the oscillating arm 61 to be closely arranged to a support axis C61.

By the way, preferably, the support axis side roller 64 fixedly supported to the oscillating arm 61 is arranged as close to the support axis C61 as possible, as shown in FIG. 2A. This is because, as shown in FIG. 4, as far the position of the support axis side roller 64 becomes from the support axis C61, the larger a travel amount M of the support axis side roller in the CD direction according to an oscillating motion of the oscillating arm becomes, and the belt member 121 becomes hard to fail off. Thus, most preferably, as shown in FIGS. 2A and 2B, the support axis side roller 64 may be arranged so that the outer circumferential surface of the support axis side roller 64 contacts a rotation center line L61 of the support axis C61.

Further, under the condition where the rotation center line L61 of the support axis C61 is in contact with the outer circumferential surface of the support axis side roller 64 as described above, preferably, as shown in FIG. 2A, the supply direction of the belt member 121 to the support axis side roller 64 may be aligned in one line in respect to the rotation center line L61 of the support axis C61. Then, a torsion of the belt member 121 that may occur by the oscillating motion of the oscillating arm 61 mainly appears as a torsion of the portion 121a of the belt member 121 to the upstream side than the support axis side roller 64, and as a result, the torsion of the belt member 121 in the downstream side than the support, axis side roller 64 is decreased.

Further, as shown in FIG. 2A, the wraparound angle of the belt member 121 to the outer circumferential surface of the oscillating end side roller 63 is preferably equal to or greater than 90 degrees, more preferably equal to or greater than 180 degrees. This is because, by making the wraparound angle large, the belt member 121 can be firmly held by the friction on the outer circumferential surface, and as a result, the falling off of the belt member 121 from the oscillating end side roller 63 can be effectively prevented. In the example in FIG. 2A, in order to make the wraparound angle approximately 180 degrees, the traveling direction of the belt member 121 is to be inverted by the oscillating end side roller 63 and then supplied to the transporting roll 50. Specifically, the belt member 121 is transported from the right of the transport roll 50 temporarily to the substantially horizontally left thereof and wrapped around the oscillating end side roller 63 that is in this position to invert the traveling direction of the belt member 121 and be alighted to a transport direction of the belt-like sheet 103b, and then the belt member 121 is supplied close to a wraparound start position Ps of the belt-like sheet 103b to the transport roll 50. In order to supply the belt member 121 in such a route, the wraparound start position Ps of the belt-like sheet 103b is positioned between the oscillating end side roller 63 and the support axis side roller 64.

Further, preferably, as shown in FIG. 2A, the oscillating end side roller 63 is preferably arranged close to the wraparound start position Ps. For example, a distance between a position Pl from which the belt member 121 separates from the outer circumferential surface of the oscillating end side roller 63 and the wraparound start position Ps is preferably made greater than 30 mm and smaller than 80 mm, in a state the line L1 of the oscillating arm 61 is facing in a direction parallel to the MD direction. This is because if the distance is long, the part of the belt member 121 separated from the oscillating end side roller 63 becomes loose like a whip when reversing the oscillating motion, and an operating delay from the oscillating end side roller 63 becomes large, and consequently, it becomes easy to slip from a target bonding position of the belt member 121 in the belt-like sheet 103b. Note that, the reason that it is better for the distance to be greater than 30 mm is because in the case where the oscillating arm 61 is short or the oscillating angle is wide, there is a possibility that, at the time of maximum oscillation of the oscillating arm 61, the oscillating end side roller 63 may move across in the MD direction in the wraparound start position Ps.

By the way, as the oscillating end side roller 63 and the support axis side roller 64, a roller with a crown is preferably used. This roller with a crown refers to a roller with the part having a maximum diameter of the roller set in the central portion in the width direction. With this roller, the belt member 121 wrapped around the outer circumferential surface is added a force toward the central portion of the roller in the width direction by the maximum diameter portion of the outer circumferential surface, and thus it does not easily fall off the roller. As an example of such a roller with a crown, for example, there is a roller that is formed with an annular rib formed along a peripheral direction in only the central portion in the outer circumferential surface, or a roller with a radius that gradually increases from the end portion toward the central portion of the outer circumferential surface, or the like.

Other Embodiments

From the above, the embodiment of this invention is described, but this invention is not limited to this embodiment and the following embodiment is possible.

Figure 5A:
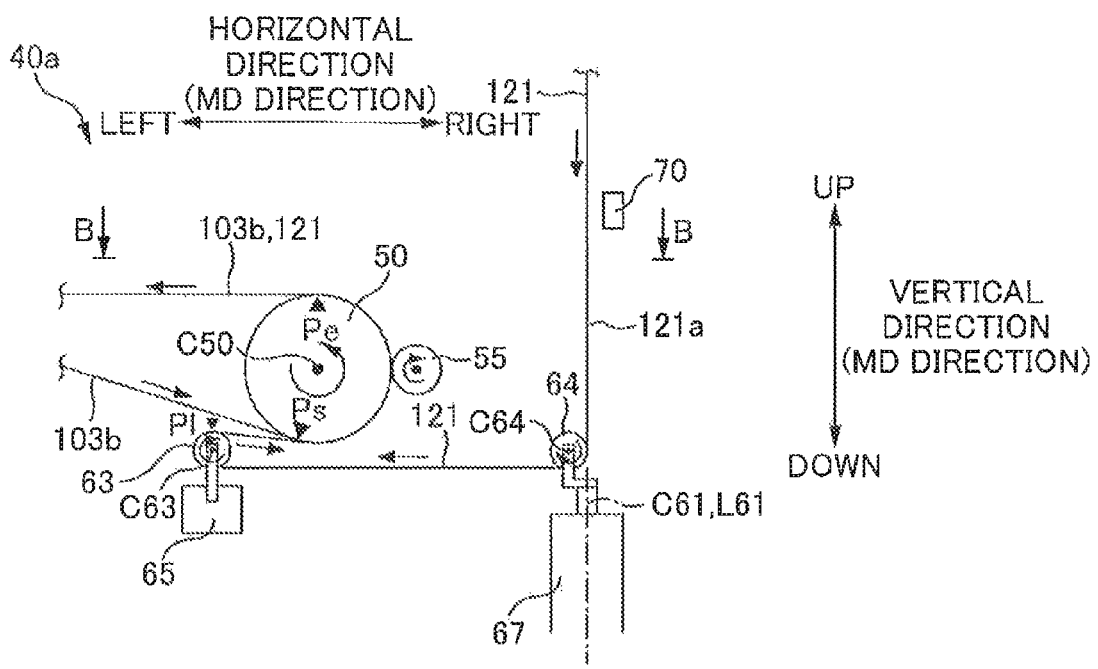
FIG. 5A is a side view of manufacturing equipment 40a of a composite sheet according to another embodiment.
Figure 5B:
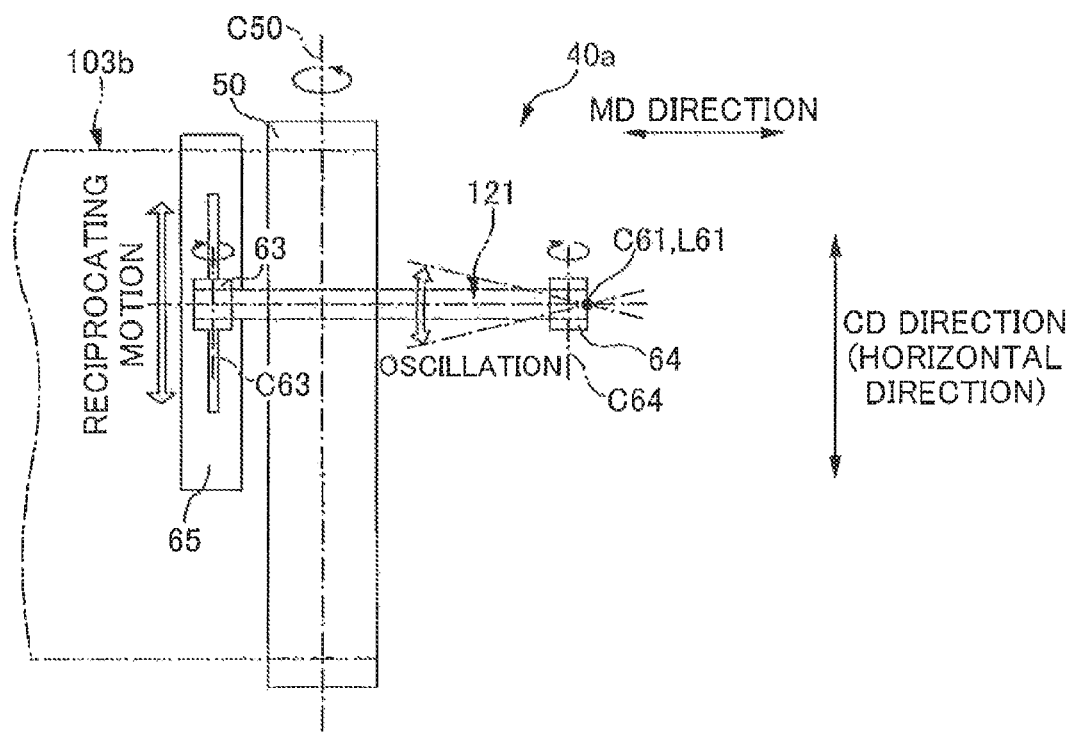
FIG. 5B is a view seen from B-B in FIG. 5A.

In the above described embodiment, a configuration of the oscillating arm 61 provided with an oscillating end side roller 63 and a support axis side roller 64 is illustrated, but the oscillating arm 61 may be omitted. Namely, as shown in FIGS. 5A and 5B, it may be a configuration having a guide member 65 such as a linear rail that guides the oscillating end side roller 63 in the CD direction so that it can reciprocate, a drive mechanism (not shown) such as a motor that makes the oscillating end side roller 63 reciprocate in the CD direction, a support member 67 that supports the support axis side roller 64 around the support axis C61 so that it can oscillate, a drive mechanism (not shown) that oscillates the support axis side roller 64, and a control portion (not shown) such as a computer that controls the drive mechanism so that an outer circumferential surface of the support axis side roller 64 faces toward the oscillating end side roller 63 in accordance with (in synchronism with) the reciprocating motion of the oscillating end side roller 63.

In the above-described embodiment, the outside sheet 3b of the back surface sheet 3 of the diaper 1 was manufactured using the manufacturing method of the composite sheet according to this invention, but it is not limited thereto, and for example, a standing gather sheet that forms a standing gather of the diaper 1 may also be manufactured. Namely, in this case, in the sheet surface of the belt-like sheet 103b, the part to which the belt member 121 is bonded stands up by the contraction of the belt member 121 and forms the standing gather.

In the above described embodiment, the manufacturing method of the composite sheet according to this invention was applied to manufacturing of a pants-type diaper 1, but it is not limited thereto and the method may be applied to manufacturing of an unfolding-type diaper (a diaper of a type in which the front torso area 1a and the back torso area 1c of the diaper are fixedly fastened by tape fasteners at the time of wearing).

In the above described embodiment, a configuration of the oscillating arm 61 provided with the two rollers of the oscillating end side roller 63 and the support axis side roller 64 is illustrated, but it is not limited thereto, and one or more of another roller may be provided between the oscillating end side roller 63 and the support axis side roller 64. Note that, in that case, the rotation axis of the added roller is preferably parallel to the rotation axis C64 of the support axis side roller 64.

In the above described embodiment, as shown in FIG. 2A, the rotation center line L61 of the support axis C61 is faced in the up-down direction (vertical direction) and the rotation axis C50 of the transport roll 50 was faced in the CD direction (horizontal direction), but if they are both, in a perpendicular relationship to each other, it is not limited thereto. That is, the rotation center line L61 of the support axis C61 is preferably perpendicular to the rotation axis C50 of the transport roll 50.

In the above described embodiment, the rotation axis C63 of the oscillating end side roller 63 and the rotation axis C64 of the support, axis side roller 64 are facing the horizontal direction, and the reason for this is for the rotation axis C50 to hand over the belt member 121 in a flat shape without any twist, in respect to the transport roll 50 facing the horizontal direction which is the CD direction. Thus, the orientations of the rotational axes C63, C64 of the oscillating end side roller 63 and the support axis side roller 64 are not limited to the horizontal direction in any way, and can be changed according to a direction to which the rotation axis C50 of the transport roll 50 faces. Namely, the rotation axis C63 of the oscillating end side roller 63 and the rotation axis C64 of the support axis side roller 64 may be arranged so that a surface depicted by these rotational axes C63, C64 according to the oscillating motion of the oscillating arm 61 is in an orientation parallel to the rotation axis C50 of the transport roll 50. Furthermore, the oscillating end side roller 63 and the support axis side roller 64 may be arranged so that the rotational axes C63 and C64 became perpendicular to the support axis C61 that is in a perpendicular relationship with the rotation axis C50 of the transport roll 50.

In the above described embodiment, the hot-melt adhesive is applied to the belt member 121 with the applying device 70, but it is not limited, thereto as long as the belt-like sheet 103b and the belt mender 121 can be bonded. For example, the adhesive may be applied to the belt-like sheet 103b, or to both the belt, member 121 and the belt-like sheet 103b. Further, instead of adhering, heat welding may be performed by such as embossing.

Figure 6:
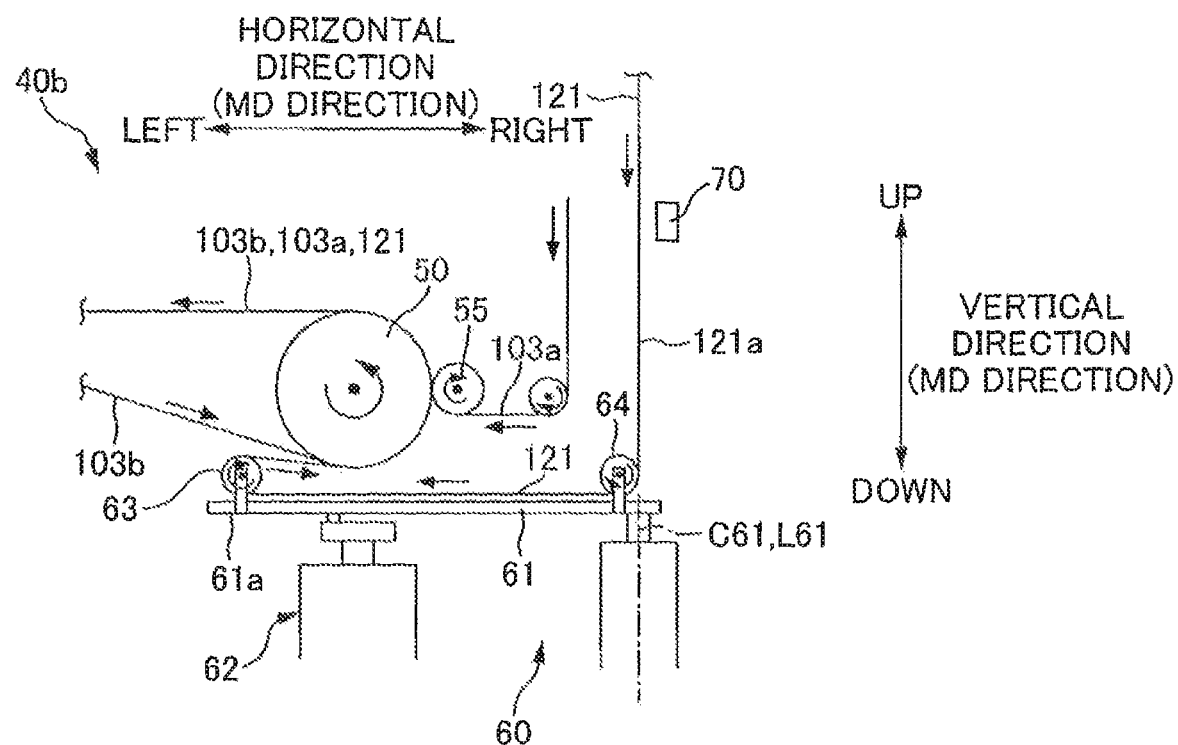
FIG. 6 is a side view of manufacturing equipment 40b of a composite sheet according to yet another embodiment.

In the above described embodiment, a separate belt-like sheet was not supplied in the position of the pressing roller 55, but as shown in FIG. 6, by supplying the belt-like sheet 103a in respect to the pressing roller 55, aside from the belt-like sheet 103b, the belt member 121 can be intervened and bonded between the belt-like sheet 103a and the belt-like sheet 103b. In this case, as shown in FIG. 6, the belt-like sheet 103a is supplied to an entry side of a gap between the pressing roller 55 and the transport roll 50, and in the gap between the rolls the belt-like sheet 103a is sandwiched and bonded to the pressing roller 55 with the belt member 121 and the belt-like sheet 103b in an overlapping state. By the way, as this belt-like sheet 103a, if a sheet material corresponding to the above described inside sheet 3a (refer to FIGS. 1a and 1b) is used, in the manufacturing apparatus 40, the back surface sheet 3 of the diaper 1 can be completed.

REFERENCE SIGNS LIST

1 disposable diaper
1a front torso area
1b crotch area
1c back torso area
2 surface sheet
3 back surface sheet
3a inside sheet
3b outside sheet
4 absorbent body
10 leg-peripheral recessed portion
11 end edge flap
12 side edge flap
16 torso-peripheral elastic member
21 front elastic belt member
22 back elastic belt member
40 manufacturing equipment of composite sheet
40a manufacturing equipment of composite sheet
40b manufacturing equipment of composite sheet
50 transport roll (bonding roll)
55 pressing roll
60 guide member 60
61 oscillating arm
61a oscillating end
62 driving source
62a motor
62b clank mechanism
63 oscillating end side roller (reciprocating roller)
64 support axis side roller (supply roller)
65 guide member
67 support member
70 applying device
103a belt-like sheet
103b belt-like sheet
121 belt member
121a portion
121e end edge
L1 line
Ps wraparound start position
Pe wraparound end position
PI position
C50 rotation axis
C61 support axis
L61 rotation center line
C63 rotation axis
C64 rotation axis
CL central line

The invention claimed is:

1. A method of manufacturing a composite sheet that continuously supplies, to a sheet surface of a belt-shaped sheet that is transported continuously in a predetermined transporting direction, an elastic belt member while reciprocating the belt member in an intersecting direction that intersects the transporting direction, and thus bonds the belt member to the sheet surface of the belt-shaped sheet while continuously changing a bonding position of the belt member on the sheet surface in the intersecting direction, the method comprising:

causing the belt member to surface contact with and bond to the sheet surface of the belt-shaped sheet, by supplying the belt-shaped sheet to an outer circumferential surface of a bonding roll that rotates in a direction along the transporting direction, and supplying the belt member via a guide member to a part of the belt-shaped sheet that is brought in contact with the outer circumferential surface of the bonding roll so that the belt member overlaps the part of the belt-shaped sheet, wherein the guide member has a reciprocating roller that reciprocates in the intersecting direction, a supply roller which is rotatable about a rotation axis and to which the belt member is supplied, and an oscillating arm;

wrapping the belt member subsequently around the outer circumferential surface of the supply roller and the outer circumferential surface of the reciprocating roller, and leading the belt member to the belt-shaped sheet; and oscillating the supply roller so that the outer circumferential surface of the supply roller faces toward the reciprocating roller in accordance with a reciprocating motion of the reciprocating roller, wherein a wraparound angle of the belt member defined by a rotation angle of the reciprocating roller when the belt member is wrapped around the outer circumferential surface of the reciprocating roller is equal to or greater than 180 degrees, the supply roller and the oscillating arm oscillate in the intersecting direction about a support axis as a rotational center of the supply roller and the oscillating arm, and the support axis is tangential to the outer circumferential surface of the supply roller when viewed along the rotation axis of the supply roller.

2. The method as claimed in claim 1, wherein
the belt member is supplied to the supply roller along the rotational center of the support axis.

3. The method as claimed in claim 1, wherein
the reciprocating roller is provided at an oscillating end of the oscillating arm, the supply roller is provided at a part of the oscillating arm closer to the support axis than the oscillating end, and the reciprocating roller reciprocates in the intersecting direction by oscillating the oscillating arm, and the supply roller is oscillated so that the outer circumferential surface of the supply roller faces toward the oscillating end of the oscillating arm in accordance with the oscillating motion of the oscillating arm.

4. The method as claimed in claim 3, wherein
the supply roller is supported on the oscillating arm in a state that the outer circumferential surface of the supply roller is facing toward the oscillating end of the oscillating arm with an orientation to the oscillating arm that is unchangeable.

5. The method as claimed in claim 3, wherein
the reciprocating roller and the supply roller are arranged on a line connecting the oscillating end and the support axis of the oscillating arm, and the reciprocating roller is supported on the oscillating arm in a state that the outer circumferential surface of the reciprocating roller is facing toward the support axis and with an orientation to the oscillating arm that is unchangeable.

6. The method as claimed in claim 3, wherein
the reciprocating roller is supported on the oscillating arm with an orientation of the outer circumferential surface of the reciprocating roller toward the oscillating end that is changeable, and the orientation is changeable in accordance with a tension from the belt member that has been wrapped around the reciprocating roller.

7. The method as claimed in claim 3, wherein
the intersecting direction is perpendicular to the transporting direction,
the support axis is perpendicular to a rotation axis of the bonding roll,
a rotation axis of the reciprocating roller and a rotation axis of the supply roller are arranged so that a surface depicted by the rotation axis of the reciprocating roller and the rotation axis of the supply roller with the oscillating motion of the oscillating arm is parallel to the rotation axis of the bonding roll.

8. The method as claimed in claim 1, wherein
each of the reciprocating roller and the supply roller comprises a central portion in a width direction of the roller, and the central portion is provided with a maximum diameter part of the roller.

9. The method as claimed in claim 1, wherein
the belt member is inverted in a traveling direction by the reciprocating roller and is supplied to the bonding roll.

10. The method as claimed in claim 9, wherein
a wraparound start position of the belt-shaped sheet to the bonding roll is positioned in between the reciprocating roller and the supply roller.

11. The method as claimed in claim 1, wherein
the intersecting direction is perpendicular to the transporting direction,
the support axis is perpendicular to a rotation axis of the bonding roll,
the reciprocating roller is arranged so that a rotation axis of the reciprocating roller is perpendicular to the support axis, and
the supply roller is arranged so that a rotation axis of the supply roller is perpendicular to the support axis.

12. A method of manufacturing a composite sheet, said method comprising:
continuously transporting a first sheet in a transporting direction;
continuously applying a second sheet to the first sheet while reciprocating the second sheet in an intersecting direction that intersects the transporting direction;
wherein said applying comprises
supplying the first sheet to an outer circumferential surface of a bonding roll that rotates in a direction along the transporting direction, and
supplying the second sheet via a guide member to a part of the first sheet that is brought in contact with the outer circumferential surface of the bonding roll so that the second sheet overlaps the part of the first sheet,
wherein the guide member has
a reciprocating roller that reciprocates in the intersecting direction,
a supply roller which is rotatable about a rotation axis and to which the second sheet is supplied, and
an oscillating arm;
wrapping the second sheet subsequently around the outer circumferential surface of the supply roller and the outer circumferential surface of the reciprocating roller; and
bonding the second sheet to the first sheet while oscillating the supply roller to continuously change a bonding position of the second sheet in the intersecting direction,
wherein a wraparound angle of the second sheet defined by a rotation angle of the reciprocating roller when the second sheet is wrapped around the outer circumferential surface of the reciprocating roller is equal to or greater than 180 degrees,
the supply roller and the oscillating arm oscillate in the intersecting direction about a predetermined support axis as a rotational center of the supply roller and the oscillating arm, and
the support axis is tangential to the circumferential surface of the supply roller when viewed along the rotation axis of the supply roller.

13. The method as claimed in claim 12, wherein
the oscillating arm has a first end where the reciprocating roller is disposed and a second end where the supply roller is disposed, and
the bonding roll is positioned between the reciprocating roller and the supply roller.

14. The method as claimed in claim 1, wherein the support axis tangential to the outer circumferential surface of the supply roller is further perpendicular to the intersecting direction and the transporting direction.

15. The method as claimed in claim 1, wherein the support axis is tangentially parallel to the outer circumferential surface of the supply roller.

16. The method as claimed in claim 15, wherein the reciprocating roller is rotatable about a rotational axis, and the rotational axis of the reciprocating roller and the rotational axis of the supply roller are parallel during said oscillating.

17. The method as claimed in claim 12, wherein the support axis tangential to the outer circumferential surface of the supply roller is further perpendicular to the intersecting direction and the transporting direction.

18. The method as claimed in claim 12, wherein the support axis tangentially parallel to the outer circumferential surface of the supply roller.

19. The method as claimed in claim 18, wherein the reciprocating roller is rotatable about a rotational axis, and the rotational axis of the reciprocating roller and the rotational axis of the supply roller are parallel during said oscillating.

* * * * *